United States Patent [19]

Meinecke et al.

[11] Patent Number: 4,937,050

[45] Date of Patent: Jun. 26, 1990

[54] APPARATUS FOR THE EVALUATION OF A TEST CARRIER FOR THE ANALYTICAL DETERMINATION OF COMPONENTS OF A BODY FLUID

[75] Inventors: Dieter Meinecke, Mannheim; Rainer Van Rijckevorsel, Brühl; Manfred Pauli, Schwetzingen; Rudolf Schüssler, Lampertheim; Thomas Jäck, Straubenhardt; Dieter Knoll, Kronberg, all of Fed. Rep. of Germany

[73] Assignee: Boehringer Mannheim GmbH, Mannheim, Fed. Rep. of Germany

[21] Appl. No.: 216,133

[22] Filed: Jul. 7, 1988

Related U.S. Application Data

[62] Division of Ser. No. 619,016, Jun. 11, 1984, Pat. No. 4,780,283.

[30] Foreign Application Priority Data

Jun. 16, 1983 [DE] Fed. Rep. of Germany ....... 3321785

[51] Int. Cl.$^5$ ...................... G01N 31/22; G01N 21/01
[52] U.S. Cl. .................................. 422/68.1; 350/529; 356/244; 356/238; 422/58; 422/63; 422/104; 422/82.05
[58] Field of Search ...................... 422/58, 68, 63, 104; 356/244, 238; 350/529

[56] References Cited

U.S. PATENT DOCUMENTS 1,882,919 10/1932 Robbins ................................. 350/529
4,372,682 2/1983 Nenninger et al. ................. 356/244
4,496,243 1/1985 Machida ............................... 356/244
4,720,372 1/1988 Fey et al. ........................... 422/68 X

FOREIGN PATENT DOCUMENTS 0037484 6/1984 European Pat. Off. .
3130749 2/1983 Fed. Rep. of Germany .
1303758 1/1973 United Kingdom .
1598086 9/1981 United Kingdom .

Primary Examiner—Robert J. Warden
Assistant Examiner—Jill Johnston
Attorney, Agent, or Firm—Felfe & Lynch

[57] ABSTRACT

According to a second aspect, the present invention also provides an apparatus for the evaluation of a flat test carrier for the analytical determination of components of a body fluid, said apparatus having a measurement unit and a positioning means, by means of which the test carrier is positioned and firmly held in a measurement position in such a manner that its test field is present in a definite position with regard to the measurement unit, wherein, for the evaluation of test carriers with a covering layer fixed in the manner of a flap on one edge of the test carrier, there is present a shutter element with a contact surface for pressing on the covering layer, the aperture element and/or the positioning means being mounted and operable in such a manner that the contact surface in the last phase of approaching the covering layer makes, relative to the test carrier, a tilting movement about a tilting axis which lies in close proximity to a fixing edge of the covering layer.

5 Claims, 6 Drawing Sheets

APPARATUS FOR THE EVALUATION OF A TEST CARRIER FOR THE ANALYTICAL DETERMINATION OF COMPONENTS OF A BODY FLUID

This is a division of application Ser. No. 619,016, filed June 11, 1984 now U.S. Pat. No. 4,780,283.

The present invention is concerned with an apparatus for the evaluation of a test carrier for the analytical determination of components of a body fluid with a measurement unit and a positioning device by means of which the test carrier is positioned and firmly held in a measurement position in such a manner that its test field is present in a definite position with regard to the measurement unit.

For the determination of components of body fluids, for example blood or urine, solid test carriers are increasingly used in clinical chemistry. In comparison with the well-known methods in which samples were mixed with liquid reagents, these processes are especially characterised by a considerably simplified carrying out. In principle, the test carrier has only to be brought into contact with the sample and then placed in a comparatively simply constructed evaluation apparatus. In this way, there can be achieved a high degree of dependability, even in the case of handling by personnel with little training. Furthermore, such apparatus can be situated decentrally where the analysis is required and the result is available without any problems in a short time.

Test carriers of a comparatively simple nature have been known for many years in the form of test strips in which a test field containing the reaction layer is applied to a longitudinal synthetic resin strip, the thickness and material of which are such that it is, in toto, flexible. Ever since it has been possible to combine the colour reaction on the test field of such test strips with a high degree of exactitude with the concentration of the component to be determined, the text strips have also been evaluated quantitatively with the help of appropriate apparatus. As a rule, this takes place by measuring the diffuse reflectivity of the test field surface after the reaction with the use of reflection photometer.

The quality and the properties of use of the apparatus employed for the evaluation are determined essentially by the means present therein for positioning the test field relative to the measurement unit of the apparatus. On the one hand, this must be such that the test carrier can be inserted as simply and problem-free as possible and can again be removed after the measurement has been carried out. However, the positioning device must, at the same time, also be able to place the test field in a precisely reproducible manner in the same place relative to the measurement unit. For a flat test carrier, such as is used in the apparatus according to the present invention, this requirement must be observed in two regards. On the one hand, an evaluable surface of the test field must be precisely positioned under the measurement unit. In this regard, high requirements are often demanded because the evaluable test field surface is very small in order, on the one hand, only to utilise the most homogeneous middle region of the test field and, on the other hand, to be able to manage with as little reagents as possible and also the smallest possible amounts of sample. In the second place, the distance between the test field surface and the measurement unit must be extremely exactly reproducible since any uncontrolled variation of this distance would falsify the measurement result. Known apparatus of the initially mentioned kind are described, for example, in European Patent Specification No. 0037484 and in British Patent Specifications Nos. 1303758 and 1598086. In the case of all of these apparatus, the positioning of the test carrier formed as a test strip in the direction of its test field surface is achieved by inserting the test strip into an appropriate canal or slot, the side walls of which guide the test strip until it comes to lie against a stop. The canal can also be used to achieve an adjustment in the direction vertical to the test field surface when it is conically shaped, as can be seen, for example, from British Patent Specification No. 1303758. In this case, however, the insertion of the test strip is difficult.

Especially advantageous test carriers, such as are described in Federal Republic of Germany Patent Specification No. 3130749, make it possible to carry out the desired analytical determinations directly on a blood sample without it being necessary previously to obtain plasma or serum by centrifuging. For this purpose, the test carrier described therein has a flat separation layer arranged on the base strip, on one end of which is applied the blood sample. The separation layer consists of glass fibre material which retains the red blood corpuscles in the region of the point of application of the blood sample. The blood plasma, on the other hand, spreads out in the layer so that, in the region of the separation layer remote from the point of application of the blood sample, a pool of plasma is available. Over this there is present at least one reaction layer which consists of a paper impregnated with reagents and is fixed on only one edge of the test carrier in the manner of a flap. Between this layer and the separation layer there can be present a hydrophobed mesh. The reaction can be simply commenced in such a test carrier, after the plasma has been obtained in the above-described manner, by applying a full-face pressure on the flap which is only fixed on one side. For the evaluation of such a test carrier, the appropriate evaluation device must have a positioning means which precisely positions the test strip regardless of whether it is or is not pressed against the measurement unit.

It is an object of the present invention to provide an improved apparatus for the evaluation of test carriers and especially its means for the reception and positioning of the test carrier in order to achieve the simplest possible handling and the highest exactitude of the evaluation.

Thus, according to a first main aspect of the present invention, there is provided an apparatus for the evaluation of a longitudinally extending, flexible test carrier for the analytical determination of components of a body fluid, the test carrier having an insertion end to be inserted into the apparatus and a handling end serving for handling thereof, said apparatus having a measurement unit and a positioning means, by means of which the test carrier is positioned and securely held in a measurement position in such a manner that its test field is present in a definite position with regard to the measurement unit, wherein the positioning means includes at least two holding means, one of which firmly holds the test carrier close to its insertion end and the other of which firmly holds the test carrier close to its handling end by means, in each case, of a fixing element, a supporting surface being provided on which the test carrier lies at least partly in its measurement position and the positioning mean includes a tensioning element by means of which the test carrier is tensioned in its measurement position along its longitudinal axis between the holding means.

The measure of holding the preferably strip-shaped test carrier under tension along its longitudinal axis on both sides provides considerable advantages in spite of apparent disadvantages with regard to the simplicity of the construction. In particular, the test strip is very precisely held in its longitudinal direction. In this way, it is, for example, possible precisely to read a magnet code applied to its rear side (i.e. on the side facing the supporting surface), after fixing. By means of this measure, it is also possible to press on the magnetic reading head for reading the magnetic code from behind with the necessarily applied pressure without having, of necessity, to exert a counterpressure on the front side of the test carrier (i.e. the side remote from the supporting surface).

The holding means can be constructed in various ways in such a manner that they have an opening position, in which they free the test carrier, and a closed position, in which they hold it. There can be used, for example, appropriate clamps which are operated magnetically or by spring pressure. According to a preferred embodiment of the present invention, the fixing element does not hold the test carrier by force locking but rather holds it in an appropriate recess of the test carrier by engaging therein in a form-locking manner. In the case of an especially simple construction, the recess is a hole provided in the test carrier close to its ends in which, in the closed position of the holding element, a pin-shaped holding element engages. In contradistinction to simple clamps, this construction has the advantage that the holding means are easy to operate and yet firmly hold the test carrier so well that, under a comparatively high tension, it can be placed in its longitudinal direction.

Instead of having a circular cross-section, the fixing pin can also have some other cross-section, the recesses in the test carrier thereby being adapted to the particular cross-sectional shape in such a manner that this is held and tensioned in a precise and reproducible manner.

The tensioning in the longitudinal direction of the test carrier can be achieved in various ways, for example by electrical means. Especially simple is a preferred embodiment in which, for example, a pneumatic or simple mechanical spring element impinges against at least one of the holding elements in the longitudinal direction of the test strip away from the middle thereof with a pretensioning. The longitudinally extending test carrier is, in the case of such a construction, preferably first fixed on the holding element associated with its insert end and then, against the prestressing, on its handling end, the holding element is brought into engagement with the corresponding recess of the test carrier. This can take place manually. However, an appropriate slider can also be provided which is preferably simultaneously able to initiate such apparatus functions which, after the fixing of the test carrier, must be initiated. The slider can also be constructed as a flap which closes the reception opening of the apparatus.

In order to simplify the insertion of the test strip and the holding of its insertion end, the appropriate holding means is, according to a further preferred embodiment, constructed in such a manner that it has a guide element for the insertion end of the test strip. The guide element preferably includes a groove narrowing conically in the direction of insertion or a corresponding slot which brings the insertion end of the test carrier into a position in which the holding element of the holding device can penetrate into the corresponding recess of the test carrier. At the same time, the guide element also provides for a guiding in a direction vertical to the surface of the test strip.

In order to bring the holding device associated with the insertion end of the test carrier from the open position into the closed position, in which its holding element engages in the recess of the test carrier, it is preferably operable from the insertion end of the test carrier. For this purpose, there can be provided, for example, a photoelement which, in the case of insertion of the test carrier, initiates an electromagnetic operation of the holding element. Especially preferred is an operating element which includes a tiltable lever device which is in operating association with a spring element. The more detailed construction can preferably correspond to the construction described in European Patent Specification No. 0037484. In this way, with simple means and without the necessity of an additional source of energy, there is achieved a dependable operation of the holding means associated with the insertion end of the test carrier. For the ejection of the test carrier, the lever device can advantageously be connected with an ejection rod, which is operated manually or with the help of adjuvant means, when the test carrier is to be ejected.

According to an especially preferred embodiment, the positioning device is so constructed that a spring-mounted pressure plate presses against the clamped test carrier approximately in the region of its test field from its rear facing the pressure surface. The pressure plate is preferably mounted in such a manner that, in the region in which, in operation, it springingly yields, it is tiltable on all sides. On the other hand, in the measurement position, the measurement unit presses preferably with aperture plate or the like from the front of the test carrier on to its test field.

By means of this construction, two important advantages are combined with one another. On the one hand, the pressure plate presses against the rear of the test field as soon as this is held in the holding position, independently of whether a counterpressure is exerted on the test field from the other side. The pressure plate can preferably be tempered. In this way, the test field is already brought to the desired temperature immediately after clamping of the test carrier. Independently thereof, it is possible first to exert pressure on the test field from its upper side at a later point of time, which is of especial importance when the above-mentioned test carrier with a flap is to be evaluated according to Federal Republic of Germany Patent Specification No. 3130749. In the second place, by means of the elastic pressure plate, different test field thicknesses and practically scarcely avoidable tolerances in the guiding of the measurement unit or of its measurement aperture can be compensated in an advantageous manner.

Preferably, the supporting surface is constructed, at least in partial regions, in a form curving convexedly away from the test carrier. From this results, independently of the more detailed construction of the curvature, a handling advantage because the handling end of the test carrier, so long as this is only held by the holding means associated with its insertion end, has a predetermined distance from the supporting surface so that the test carrier can be easily inserted and taken out. The curved supporting surface also simplifies the pressing of the handling end of the test carrier, in the manner described hereinbefore, with the help of a slider via the spring-loaded holding element in the longitudinal direction of the test carrier, bringing its recess into engagement with this.

A curved supporting surface is also especially advantageous when the test carrier carries on its rear side a magnetic code which is to be read off by an appropriate reading head. In order to achieve the necessary close contact between the slot of the reading head and the magnetic coating of the test carrier, the supporting surface for the test carrier and the path of movement of the reading head relative to this is so constructed that the apex of the reading head at that point of its path of movement is higher than the supporting surface of the test strip. It is thereby achieved that, on every part of the path of movement, the tensional forces acting upon the test strip produce a component in the direction of the reading head. In principle, this can also be achieved with a completely straight-running supporting surface, from which the reading head projects slightly. However, a better pressing on between the magnetically coated surface and the reading head is achieved when the supporting surface is comparatively curved in the region of the path of movement of the reading head and the reading head projects slightly.

Constructively, a solution is especially simple in which the positioning device is, in its totality, tiltable about a tilting axis and in which the magnetic reading head is mounted fixedly on the apparatus. The supporting surface thereby runs in the region of the relative path of movement of magnetic layer and reading head circularly around the tilting axis and has a slot through which the reading head projects slightly with regard to the supporting surface. Since, in the case of this construction, the magnetic reading head is fixedly positioned on the apparatus, it can be provided especially simply with an adjustment device. The positioning device, which in toto is tiltable, can be advantageously so arranged in the apparatus as a whole that the test strip can easily be gripped in the holding means in an end position of the tilting path, whereas in the other tilting position, the test field is brought into contact with the measurement unit and is evaluated. During the movement from the first into the second end position, the reading of the magnetic code takes place. This coding contains, in particular, data regarding the charge-specific evaluation curve, i.e. in the case of a reflection-photometric evaluation, the functional relationship between the measured diffuse reflectivity and the concentration of the substance to be determined in the sample. In addition, further information can also be given, especially regarding the process conditions to be maintained by the apparatus, for example the temperature and measurement time.

According to a second main aspect of the present invention, it concerns an apparatus of the initially described kind which is especially constructed for the evaluation of the types of test carriers already mentioned, which have a covering layer in the manner of a flap fixed on one edge of the test carrier. As already mentioned, special embodiments of such test carriers are described in Federal Republic of Germany Patent Specification No. 3130749. It is here an important feature that the pressing of the covering layer on to the test carrier takes place in such a manner that the inclusion of bubbles between the covering layer flap and the plasma pool present thereunder is avoided as far as possible.

In order to achieve this object, the apparatus according to the present invention has a aperture element with a contact surface for pressing on the covering layer, the aperture element and/or the positioning device thereby being mounted and operable in such a manner that the contact surface, in the last phase of the approach to the covering layer, makes a tilting movement about a tilting axis relative to the test carrier, which tilting axis is in close proximity to the fixing edge of the covering layer.

The aperture element is, in the simplest case, a metal part with a flat lower contact surface which is brought into contact with the flap of the test carrier and with a circular hole, which serves as a window, through which the coloration of the test layer connected to the flap can be evaluated optically. By means of the described movement, it is achieved that the pressure in the case of pressing the contact surface of the aperture element against the flap is uniformly propagated in the region of the test field, with the avoidance of air inclusions.

Especially preferably, the aperture element is mounted and operable in such a manner that the contact surface in the last phase of the approach to the test carrier flap makes a sliding relative movement away from the fixing edge of the flap. In this way, the danger of air inclusions is till better avoided and the flap is pressed against in an especially uniform manner.

It is to be stressed that the solution according to the second main aspect of the present invention is advantageously used in combination with that according to the first main aspect but, independently thereof, is also of importance.

The complicated movement of the aperture element relative to the test carrier can, in principle, be realised with the help of appropriate servo drives and electronic controls in various ways. However, in practice, the necessary dependability and the cost-favourable construction is to be taken into account. It is thereby especially advantageous when, for the case in which the whole positioning means is tiltable in the above-described manner, the same drive is also used for pressing on the test carrier flap. In this sense, it is advantageous when the aperture element is connected via a coupling mechanism with the drive for the positioning means. Especially advantageously, the aperture element is, in operation, a part securely connected with the measurement unit, the mentioned drive thereby driving the positioning means and the measurement unit via the coupling mechanism in such a manner that the desired relative movement between the positioning means and the measurement unit is achieved.

Practically suitable are here all coupling mechanisms which work sufficiently free of play, are simply constructed and do not require too much force. In particular, there can be used an appropriate link guiding. Especially preferred, because it is particularly simply constructed and is dependable in function, is a coupling mechanism which has two interengaging toothed rims which, via corresponding, for example, sector-shaped connecting parts, are connected, on the one hand, with the measurement unit and, on the other hand, with the positioning means. The two toothed rims run circularly about two tilting axes about which are tilted, on the one hand, the constructional unit of the positioning means and, on the other hand, the constructional unit of the measurement unit.

A part of the constructional unit carrying the positioning means forms the pressure plate, the surface of which facing the test carrier preferably runs substantially tangentially to the curvature of the supporting surface and passes over smoothly into this. The contact surface of the aperture element, which is provided for pressing on the flap of an appropriate test carrier, preferably does not run vertically to the radius crossing its middle about the tilting axis of the constructional unit carrying the measurement device. On the contrary, it is preferably so orientated that a vertical on the contact surface runs on the side of the tilting axis of the measurement device remote from the positioning means. The toothed rim associated with the measurement unit preferably has a smaller diameter than the toothed rim associated with the positioning means.

By means of this method of construction, there is achieved a simple and dependable coupling of the two constructional units. By means of experiments, such an arrangement of the constructional parts can readily be determined that the mentioned geometric conditions in the case of the coming close of the measurement aperture with its contact surface to the flap of the test carrier are fulfilled.

As mentioned above, the apparatus according to the present invention is especially suitable for the evaluation of test carriers of the kind described in Federal Republic of Germany Patent Specification No. 3130749. The mentioned advantages of the individual constructional features are hereby combined with one another in an ideal manner. Due to the clamping of the strip-shaped test carrier between the holding means, this is precisely positioned. At the same time, the pressure plate presses from behind against the test carrier in the region of the test field and begins to temper this. This is possible while, at the same time, still no pressure is exerted from the opposite side on the test field. In this time, the plasma-obtaining phase takes place in the manner described hereinbefore. At a point of time related to the test in question and with an appropriate speed, the constructional unit carrying the positioning means is then tilted from its first position into the second position, whereby a preferably magnetic coding present on the rear side of the test carrier can be read off. The course of movement can be readily controlled in such a manner that, at a predetermined point of time, the measurement unit with the measurement aperture presses over its contact surface on the flap of the test carrier and thus the reaction is initiated. Insofar as it is desired, a ventilation phase can also be provided in which the measurement unit is again tilted back in order to take the pressure from the test field and to expose this to a ventilation. Finally, at a further predetermined point of time, the contact surface of the measurement shutter is pressed with the measurement unit against the test field and the measurement is carried out.

Further advantages and features important for the present invention are to be gathered from the embodiments described hereinafter in more detail, with reference to the accompanying drawings, in which.

Figure 1:
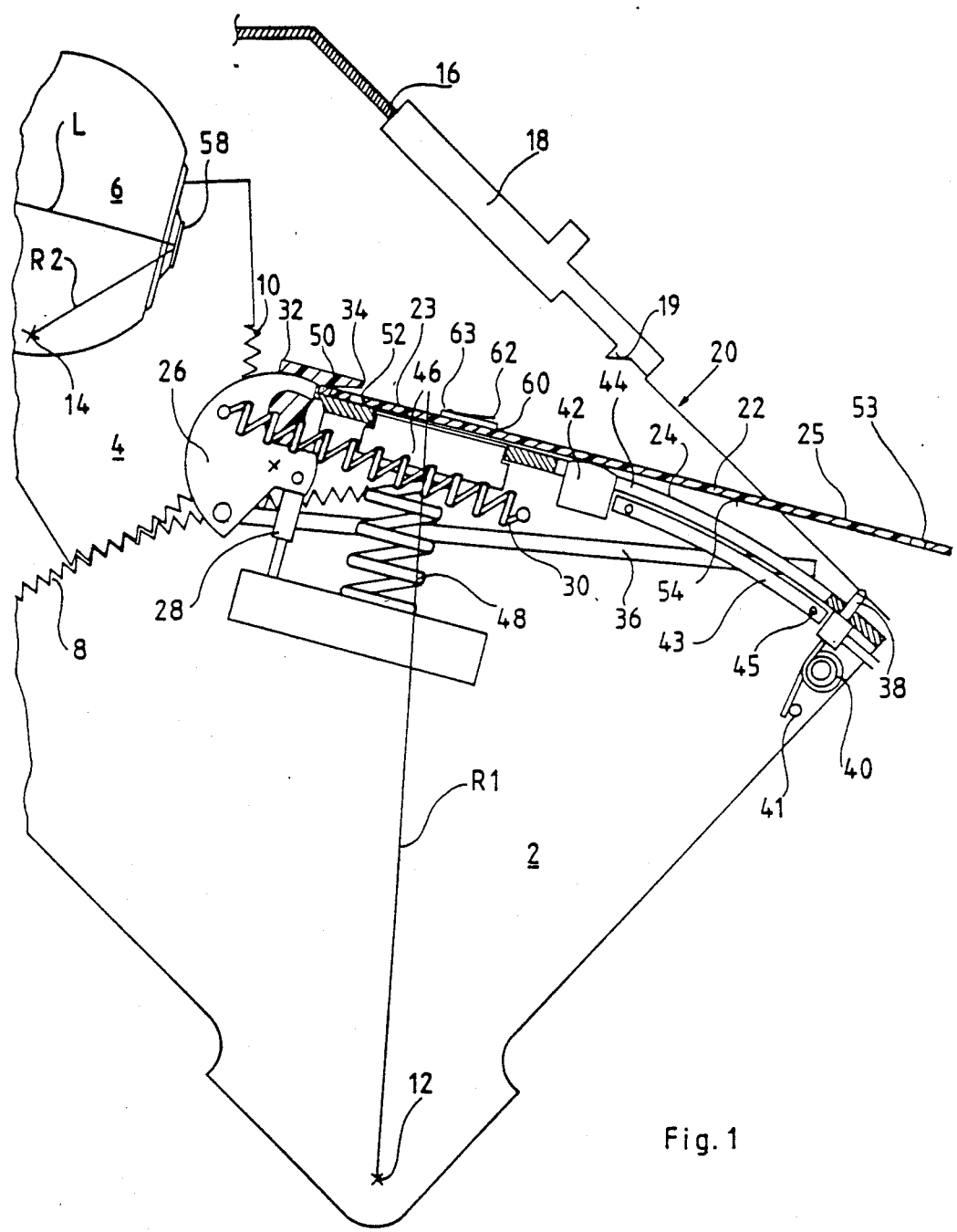
FIG. 1 is a schematic illustration of a part of an apparatus according to the present invention, especially of the constructional units carrying the measurement unit and the positioning means, a test strip-shaped test carrier having just been inserted.

FIG. 1 shows schematically a side view of the device with a reception slider 2 carrying the positioning means and a carrier slider 4 for a measurement unit 6. The measurement unit is here constructed as an Ulbricht's sphere by means of which the diffuse reflection is measured reflection photometrically from an illuminated test field. Within the scope of the present invention, there can, of course, be used other measurement units. The reception slider 2 and the carrier slider 4 have sector-shaped parts which, on their end surfaces, have interengaging toothed rims 8, 10. The two sliders 2, 4 are tiltable about axes of rotation 12, 14, a direct coupling of the movement taking place because of the toothed rims. The two sliders, each with the parts fixed thereto, form tiltable constructional units. For the tilting of the reception slider and thus also of the carrier slider, there is provided an electric motor (not illustrated). On a housing 16, which is here only indicated, there is provided a displaceable flap 18, by means of which a reception opening 20 can be closed. Through the reception opening 20, there can be inserted a test carrier, constructed as a test strip 22, with its insertion end 23. The device with the reception slider 2 and the carrier slider 4 is arranged on a frame within the housing 16. In the region of the reception opening, the reception slider 2 has a curved supporting surface 24 for the test strip 22; an unimpeded insertion of the test strip 22, firmly held on its handling end 25, is possible without difficulty.

Furthermore, the reception slider 2 contains an operational element in the form of a lever device constructed as a cam plate 26, with which a stop pin 28 is coupled. With the front end 50, the test strip 22 lies against the upper end of the cam plate 26. By means of a spring element 30, the cam plate is impinged against by a force not only in the first end position illustrated in FIG. 1 but also in the second end position illustrated in FIGS. 2 to 4, in each case in the direction away from an apex of the tilting path lying between the two end positions. In the region of the stop pin 28, there is also present on the reception slider 2 a guide element 32 with a guide slot 34 for the test strip 22. The guide slot runs slightly conically not only in the plane of the drawing but also in a plane vertically thereto. The guide element 32 thereby guides the insertion end 23 of the test strip 22 into the position in which the stop pin 28 can penetrate into the corresponding recess 52 of the test strip 22. Furthermore, with the cam plate 26 there is also connected an ejection rod 36. On the other end of the reception slider 2, there is present a second holding means for the test strip 22. This includes, as holding element, a tension pin 38 which is impinged against by a spring 40 which is supported on a countermounting 41.

In the region of the supporting surface 24, there is secured on the frame a reading head 42 for a magnetic code applied to the rear 54 of the test strip 22. The supporting surface 24 of the reception slider 2 has, for the reader head 42, a slot 44 extending in its longitudinal direction. The slot 44 is essentially closed by means of a slide 43 in the illustrated position of the reception slider 2. The slide 43 is movable in the reception slider 2 on bolts 45 arranged vertically to the plane of the drawing. By means of a mechanism (not illustrated), the slider 43 can be moved to the side for freeing the slot 44 for the reading head 42 in the case of tilting the reception slider 2. The reading head 42 projects at a predetermined distance over the supporting surface 24 for the test strip. Finally, a pressure plate 46 is provided in order to give, in the measurement position, a definite pressing-on pressure and, furthermore, also a plane-parallel positioning of the test field. The associated spring element 48 has a progressive spring characteristic for the tolerance equilibration.

Figure 2:
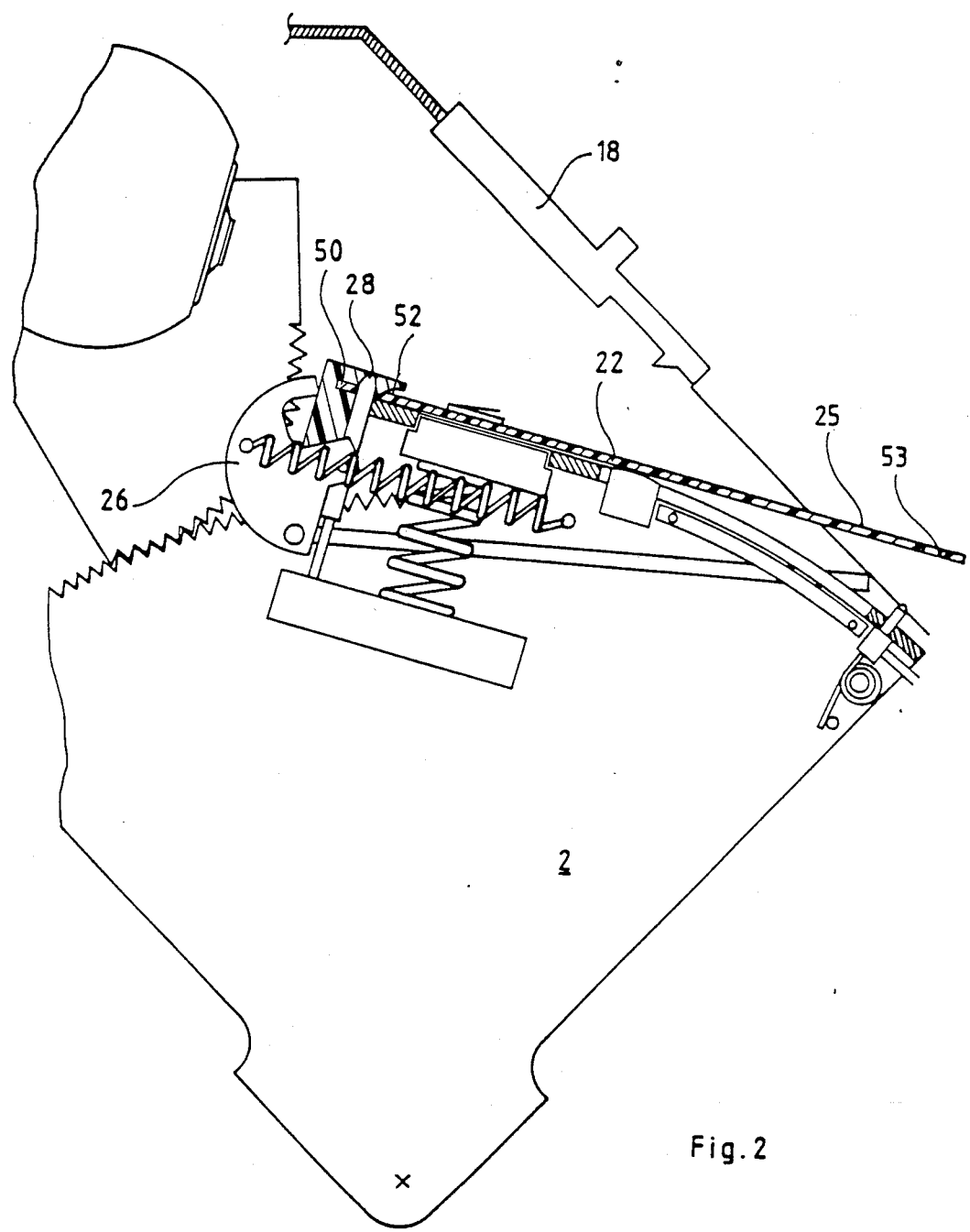
FIG. 2 is the device according to FIG. 1 in which the holding means associated with the insertion end of the test carrier is present in its closed position.

FIG. 2 shows the device with a fully inserted test strip 22. By means of the front end 50 of the test strip 22, the cam plate 26 is tilted into the illustrated position. Details thereof are given in European Patent Specification No. 0037484. The stop pin 28 was hereby moved upwardly and it now engages in a recess 52 of the test strip. The insertion end 23 of the test strip 22 is consequently positioned in a definite manner on the reception slider 2.

Figure 3:
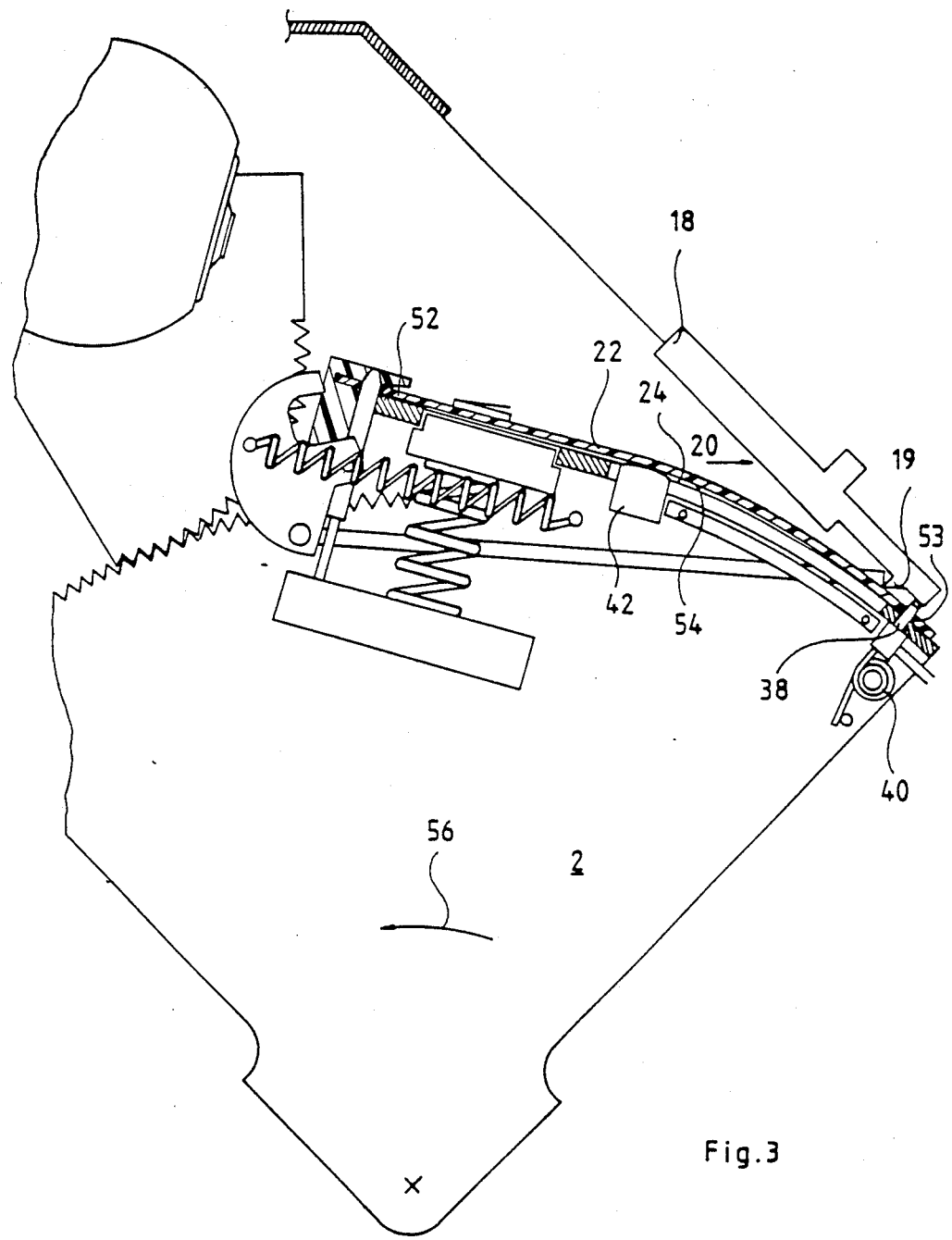
FIG. 3 is the device according to FIG. 1 with a completely inserted test carrier gripped between two holding means.

In FIG. 3, there is illustrated the flap 18 in the position closing the reception opening 20. In the case of pushing down the flap 18, with the help of a corresponding projection 19, the test strip 22 is also pressed on the curved supporting surface 24. The tension pin 38 was also inserted simultaneously into a further recess 53 of the test strip 22. As can be seen, the spring 40 impinges against the tension pin 38 with a force in the longitudinal direction of the test strip away from its middle so that a corresponding pulling force acts on the test strip 22 and this is thus firmly tensioned on the reception slider 2. The reading head 42 projects somewhat over the supporting surface 24, a good embracing by the test strip 22 thereby being obtained. On the rear 54 of the test strip 22, there is present a magnetic layer which contains binary coded data. These data are, in the case of tilting the slider in the direction of the arrow 56, automatically read and correspondingly evaluated in an appropriate electronic device.

Figure 4:
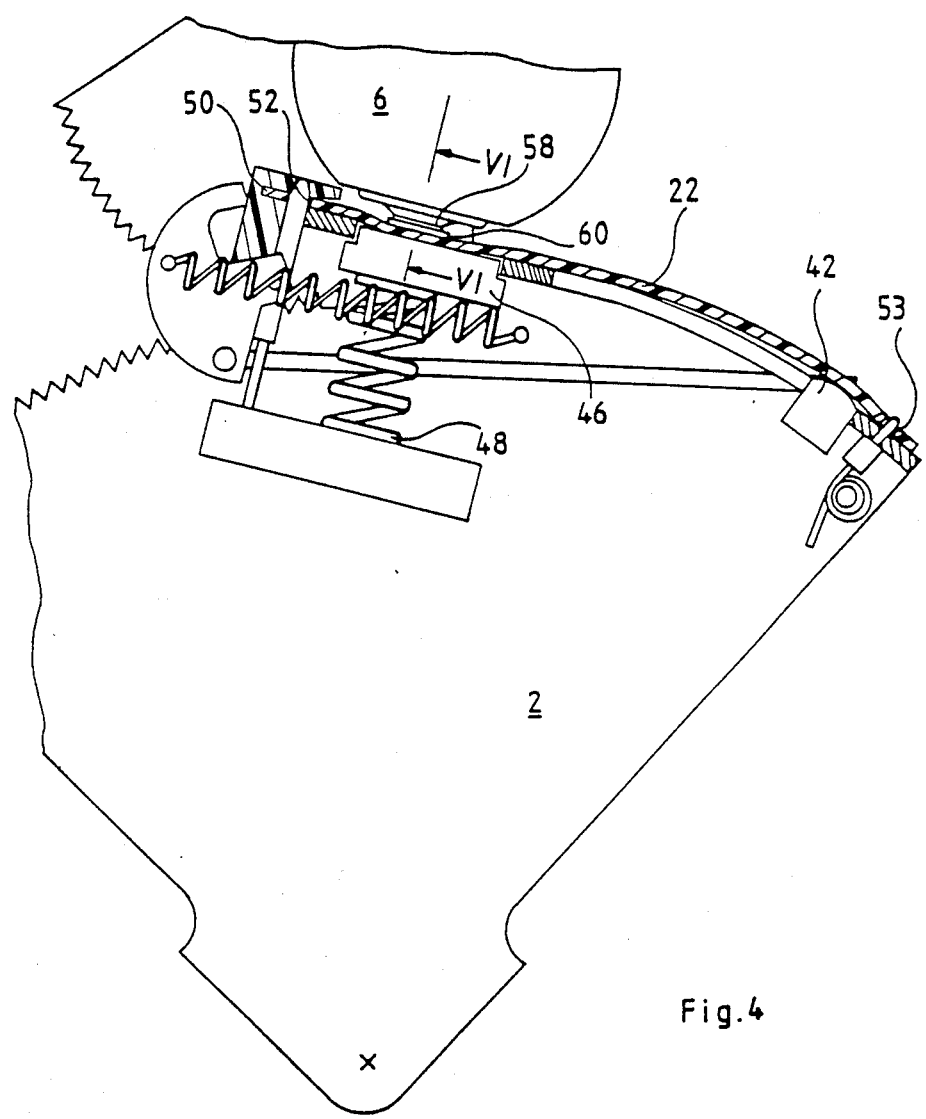
FIG. 4 is the device according to FIG. 1 in which the positioning means and the measurement unit are present in the measurement position.

FIG. 4 illustrates the end position of the tilting movement. It can be seen that, by means of tilting the reception slider 2 with regard to the positionally-fixed reading head 42, this is present, after the tilting procedure, on the handling end of the test strip 22, i.e. the magnetic reading head has, during the tilting movement, passed over the whole of the part of the test strip 22 covered with a magnetic layer.

FIG. 4 shows the reception slider 2 and the measurement unit 6 in the measurement position. The measurement shutter 58 lies in a defined manner on the measurement field 60 of the test strip, a predetermined pressing-on pressure thereby being maintained via the pressure plate 46 and the spring element 48.

Figure 5A:
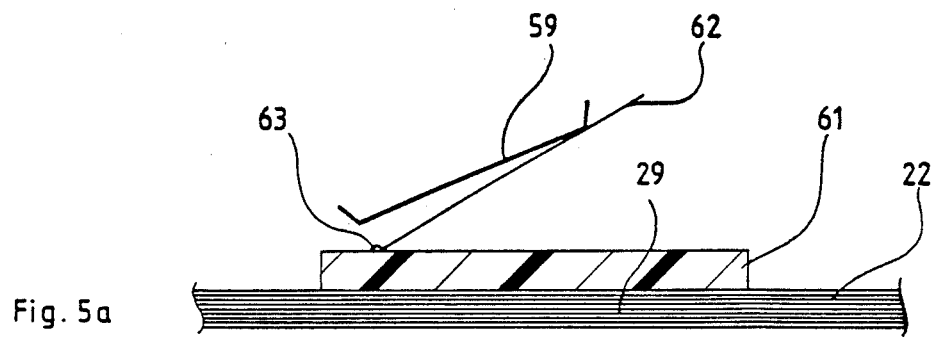
FIGS. 5a to 5c are schematic illustrations of the courses of movement in the case of pressing a test carrier flap on to the test carrier.
Figure 5B:
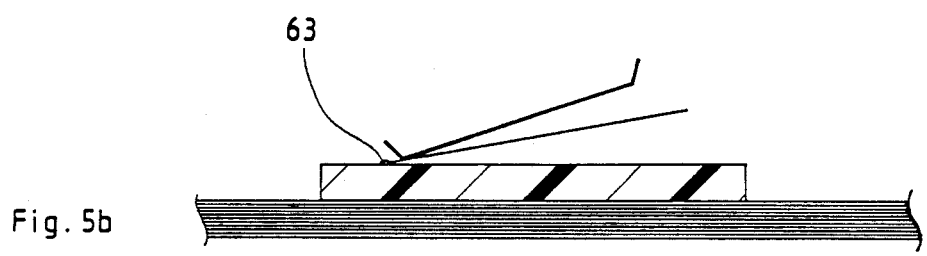
Figure 5C:
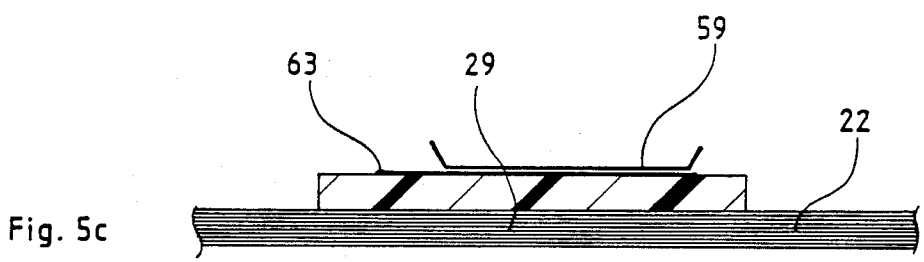

FIG. 5 show schematically, in a greatly enlarged illustration, various phases of the movement of the contact surface 59 of the shutter 58 in the case of coming close to the test strip 22, this thereby forming a positionally fixed illustrated reference point. There can be seen a plasma-obtaining layer 61 on the base strip 29 of the test strip 22, lying full-facedly. Above this, there is present a covering layer, which is rectangular in plane view, constructed as a flap 62, only one edge 63 of which is attached to the base strip 29 (in the illustrated embodiment via the plasma-obtaining layer 61). In the movement phase illustrated in FIG. 5a, one edge of the contact surface 59 has just contacted the flap 62 and begins to press this downwardly. In FIG. 5b, the flap 62 is present in a position shortly before it comes into contact with the plasma-obtaining layer 61. In FIG. 5c, the contact surface 59 lies completely on the flap 62 and this on the plasma-obtaining layer 61. It can be seen that the contact surface 59 performs a movement which is essentially composed of two components, namely, a tilting movement and a movement in a direction parallel to the surface of the test strip 22 away from the fixing edge 63 of the flap 62. The tilting movement has, in the illustrations in FIG. 5, in which, as mentioned, the reference system moves with the test strip 22 so that this appears positionally fixed in the Figure, no fixed tilting axis. As is to be seen from the Figures, however, the tilting axis moves in the illustrated approaching phase in any case in the proximity of the fixing edge 63 of the flap 62 and runs substantially parallel to this. It thereby results that, in the last phase of the coming close, the pressure exerted by the contact surface 59 on the flap away from its fixing edge thus, in the illustration in FIG. 5, increases from left to right. In this way, air inclusions are avoided. It is thereby not harmful that, as is to be seen in FIG. 5a, at the commencement of the approaching phase, the contact surface 59 first contacts the flap 62 on the end remote from the fixing edge 63. The only thing which is decisive is that the described tilting movement is realised in the last phase of the approaching (FIG. 5b, FIG. 5c). An even more uniform pressing of the flap 62 against the plasma-obtaining layer 61 is achieved by the described movement components parallel to the surface of the test carrier in FIG. 5 from left to right.

The course of movement described with reference to FIG. 5 can be realised, in the case of a construction such as is illustrated in FIGS. 1 to 4, in that the pressure plate 46 and the measurement aperture eleme 58 are arranged relative to the radii (R1, R2) in each case crossing their middle, of the associated tilting axes 12 or 14, in appropriate manner, the momentary movement in the approaching phase thereby being determined not only by the tilt of the pressure plate 46 or of the measurement aperture element 58 to the radii in question but also by their distance from the tilting axis. Which arrangement is to be chosen in a particular case can be determined with the help of the principles of gears by drawing or by optimisation experiments. A construction of the illustrated type which has proved to be especially advantageous is one in which the pressure plate 46 continues substantially tangentially the curvature of the supporting surface 24 and in which the contact surface 59 of the measurement aperture 58 is so tilted against the radius (R2) crossing its middle about which the associated tilting axis 14 is inclined that a vertical (L) runs on the contact surface 59 on the side of the tilting axis 14 remote from the reception slider 2.

Figure 6:
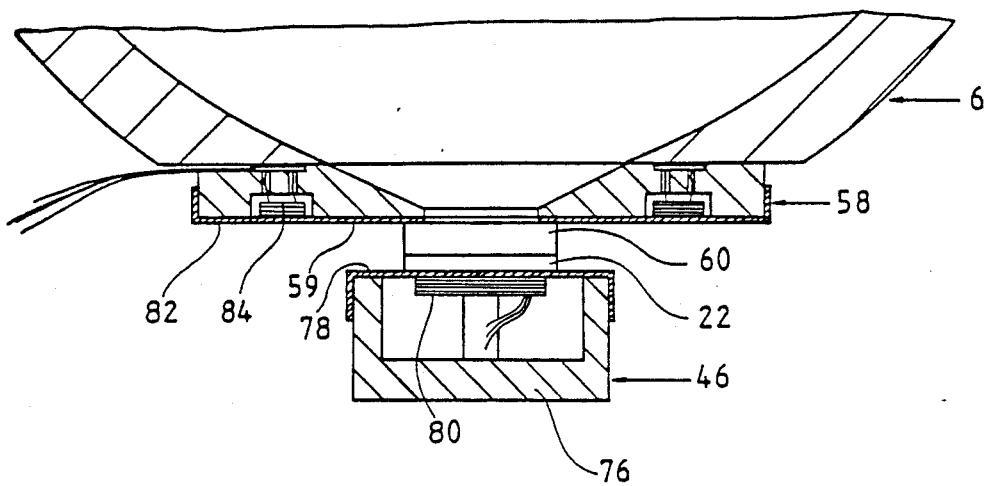
FIG. 6 is a cross-section view along the line VI—VI in FIG. 4.

FIG. 6 shows, on an enlarged scale, the lower part of the measurement unit 6 with the aperture element 58. There is also to be seen a carrier 76 with a heating plate 78, which are parts of the pressure plate 46. Between the heating plate 78 and the measurement shutter 58 is to be seen the test strip 22 with the test field (consisting of the plasma-obtaining layer 61 and the flap 62), the test strip 22 thereby extending vertically to the plane of the drawing. The heating plate 78 is a part of a heating device which has a heating element 80. On the measurement aperture element 58 there is also arranged a heating plate 82 with heating elements 84. It is especially advantageous that the pressure plate, even in the case of the phase illustrated in FIG. 3, i.e. as soon as the test strip 22 is gripped between the two holding means, is pressed from behind in the region of the test field 60 against the test strip 22. In this way, a pretempering is possible even in this phase and thus possibly a comparatively long time before the measurement unit 6 with the measurement aperture 58 is pressed from the front side against the test field 60 (FIG. 4). In this way, a pretempering is possible, which leads to an increase of the tempering exactitude and/or to a considerable saving of time.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. An apparatus for the evaluation of a flat test carrier, said test carrier including a covering layer fixed as a flap on one edge of the test carrier, comprising a positioning means which positions and firmly holds said test carrier in a measurement position against a measuring unit which comprises an aperture element with a contact surface which contacts the covering layer of said test carrier, at least one of said aperture element and said positioning means being pivotally mounted to contact said contact surface of said aperture element and said covering layer of said test carrier held in said positioning means by pivoting said at least one of said positioning means and said aperture element about a pivoting axis which lies in close proximity to the edge of said test carrier held in said positioning means.

2. The apparatus according to claim 1 wherein said at least one of said aperture element and said positioning means further comprises means to translate said contact surface of said aperture element in a plane parallel to the surface of said test carrier held in said positioning means away from the edge of said test carrier.

3. The apparatus according to claim 1 wherein said aperture element and said measuring unit are connected to a driving means by a coupling mechanism and wherein said driving means operates both said measuring unit and said positioning means.

4. The apparatus of claim 3 wherein said positioning means further comprises a supporting surface having first gear means and wherein said coupling mechanism of said measuring unit further comprises second gear means engageable with said first gear means and wherein when said at least one of said aperture element and said positioning means pivots towards the other of said aperture element and said positioning means, said first gear means and said second gear means engage to bring said measuring unit into contact with said test carrier held in said positioning means whereby said supporting surface and said contact surface of said aperture element contact securely along a longitudinal axis of said test carrier held in said positioning means.

5. The apparatus according to claim 4 wherein said second gear means comprises a smaller diameter than said first gear means.

* * * * *